(12) United States Patent
Röhrig

(10) Patent No.: US 8,703,052 B2
(45) Date of Patent: Apr. 22, 2014

(54) METHOD FOR DISINFECTING A BOTTLE

(75) Inventor: Peter Röhrig, Vienna (AT)

(73) Assignee: MAM Babyartikel Gesellschaft M.B.H., Vienna (AT)

( * ) Notice: Subject to any disclaimer, the term of this patent is extended or adjusted under 35 U.S.C. 154(b) by 205 days.

(21) Appl. No.: 13/256,470

(22) PCT Filed: Jan. 13, 2011

(86) PCT No.: PCT/AT2011/000018
§ 371 (c)(1),
(2), (4) Date: Sep. 14, 2011

(87) PCT Pub. No.: WO2011/094773
PCT Pub. Date: Aug. 11, 2011

(65) Prior Publication Data
US 2012/0027641 A1 Feb. 2, 2012

(30) Foreign Application Priority Data
Feb. 8, 2010 (AT) .................................. A 175/2010

(51) Int. Cl.
*A61L 2/08* (2006.01)
*A61J 11/00* (2006.01)
(52) U.S. Cl.
USPC ...... 422/26; 422/1; 422/27; 422/28; 215/11.1
(58) Field of Classification Search
USPC .......... 422/1, 26–28, 307; 215/11, 11.1, 11.3; 137/845
See application file for complete search history.

(56) References Cited

U.S. PATENT DOCUMENTS

| 2,610,755 | A | | 9/1952 | Gits |
| 3,134,495 | A | * | 5/1964 | Carbonel ..................... 215/11.5 |
| 5,499,729 | A | | 3/1996 | Greenwood et al. |
| 2007/0068890 | A1 | * | 3/2007 | Rohrig ......................... 215/11.1 |
| 2009/0184080 | A1 | | 7/2009 | Klaver et al. |

FOREIGN PATENT DOCUMENTS

| AT | 501 841 A1 | 11/2006 |
| AT | 009 807 U1 | 4/2008 |
| FR | 2769841 A1 | 4/1999 |
| GB | 2 395 108 A | 5/2004 |
| WO | 99/11218 A1 | 3/1999 |
| WO | 2005/041851 A2 | 5/2005 |

OTHER PUBLICATIONS

International Search Report: mailed Apr. 4, 2011; PCT/AT2011/000018.
Austrian Search Report: mailed May 27, 2010; 4A A 175/2010-1.
Written Opinion of Internation Searching Authority dated Aug. 14, 2012.

* cited by examiner

*Primary Examiner* — Monzer R Chorbaji
(74) *Attorney, Agent, or Firm* — Ladas & Parry LLP

(57) ABSTRACT

A method for disinfecting a bottle, in particular a baby bottle, including a bottle jacket which is open on both ends, wherein, in a dispensing position, a bottom cap is fastened to a bottom-side opening and a teat is fastened to a teat-side opening by a fastening ring, the inner periphery of the bottom-side opening being larger than the outer periphery of the fastening ring, wherein, for transfer into a disinfection position, the bottom cap is removed from the bottle jacket, the teat and the fastening ring are placed onto the bottom cap and introduced into the bottle jacket, the bottom cap is attached to the bottom-side opening, a disinfectant is filled into the bottle jacket before the bottle is heated for disinfection.

10 Claims, 4 Drawing Sheets

METHOD FOR DISINFECTING A BOTTLE

The invention relates to a method for disinfecting a bottle, in particular a baby bottle, including a bottle jacket which is open on both ends, wherein, in a dispensing position, a bottom cap is fastened to a bottom-side opening and a teat is fastened to a teat-side opening by a fastening ring, the inner periphery of the bottom-side opening being larger than the outer periphery of the fastening ring.

Various methods and devices for disinfecting and/or sterilizing bottle bodies of, in particular, baby bottles provided with bottle teats have been known from the prior art. Such devices are usually referred to as sterilizers, although those devices actually perform just a disinfection (=bacterial count reduced by a factor $10^5$) rather than a sterilization (=bacterial count reduced by a factor $10^6$). In the following, the terms are, however, used synonymously, meaning a bacterial count reduction by a factor of at least $10^5$.

In addition, numerous baby bottles are known, which comprise bottle jackets that are open on both ends, with the bottom-side openings having larger peripheries than the teat-side openings. A baby bottle of this type is thus, for instance, known from WO 2005/041851 A2 in the name of the present applicant, wherein, in that case, the comparatively large bottom-side opening is, in particular, provided to enable the provision of a large bottom-side air-intake valve. A similar baby bottle having a comparatively large bottom-side opening relative to the teat-side opening is known from DE-8704733 U. WO 99/011218 discloses a further baby bottle having a jacket that is open on both ends and on which a nipple part or bottom cap is screwed.

As a rule, such baby bottles are sterilized or disinfected in devices especially provided for this purpose.

From DE-3149754 A, a sterilization or disinfection device is, for instance, known, in which several reception means for baby bottles as well as separate reception means for bottle teats are provided. That device involves the drawback that, in particular, only one comparatively large disinfection volume is provided such that the bottles are merely partially disinfected after the disinfection procedure, with a rather inhomogeneous disinfection level having been achieved. Moreover, acquisition costs are relatively high, and the space demand of such devices is also relatively large.

From GB-2395108 A, a further sterilization device for cleaning a baby bottle is known, which involves the drawbacks described in connection with DE-3149754 A. The device comprises a container containing a water bath. The elements of the baby bottle are placed in the water bath, which can be excited to vibrate by using a sound generator. The elements to be cleaned may, moreover, be exposed to UV radiation.

A baby bottle especially designed for disinfection purposes is known from GB-2324788 A. It discloses a baby bottle in which a teat, a fastening ring and a cover cap can be arranged in a food-dispensing position and in a disinfection position. It comprises, however, a bottle body that is closed on its bottom end such that, for disinfection purposes, the teat and the fastening ring can only be received in a chamber to be closed by the cover cap. In order to enable the teat to be held in a disinfection position spaced-apart from the bottle body, various specifically designed stowing and holding means are required, which is disadvantageous.

FR-2769841 A1 discloses a further baby bottle closed on its bottom side, which, for disinfecting the teat, is connected with a closure cap to be screwed onto the container jacket. In the interior of the closure cap, a disinfection volume is provided for the teat.

By contrast, it is the object of the present invention to provide an energy- and time-saving method for disinfecting bottles of the initially defined kind, and to provide a special use of such bottles, requiring neither specifically designed means for disinfection nor specifically designed holding means for positioning the teat in a disinfection position spaced-apart from the bottle body.

In accordance with the invention, this is achieved in that, for transfer into a disinfection position, the bottom cap is removed from the bottle jacket, the teat and the fastening ring are placed onto the bottom cap and introduced into the bottle jacket respectively, the bottom cap is attached to the bottom-side opening, a disinfectant, particularly water, is filled into the bottle jacket before the bottle is heated for disinfection. It has been shown in a surprising manner that—provided the usually circular bottom-side opening of the bottle body is larger than the usually substantially circular outer periphery of the fastening ring—both the teat and the fastening ring can be received in the interior of the bottle jacket upon removal of the bottom cap from the bottle body, preferably after having placed these two parts onto the bottom cap. Thus, sort of a disinfection chamber is formed in the interior of the bottle jacket after the bottom cap has been refastened to the bottom-side opening such that, after a disinfectant, usually water, has been filled into the disinfection chamber, it is brought to boiling and evaporating by heating so as to readily enable the reliable disinfection of all parts of the bottle, i.e., in particular, the bottle jacket, the bottom cap, the fastening ring and the teat. Neither a device specifically configured for disinfection purposes nor additional holding means or the like are required to this end. The user is thus offered an extremely simply handleable method for disinfecting bottles, and a novel use of baby bottles already known per se. In addition, the method is comparatively energy- and time-saving, since only those surfaces are sterilized which come into contact with food or the infant's mouth. Thus, in particular, the inner surfaces of the bottle parts (bottle jacket, bottom cap and fastening ring) as well as the entire teat, i.e. its inner surface and the mouth-contacting surfaces, are sterilized using a comparatively small amount of disinfectant. A disinfection of the outer surfaces, which is not necessary from a hygienic point of view, yet would require an extremely high energy consumption, can be obviated.

It will be of particular advantage, if the fastening ring along with the teat are placed onto the bottom cap, and introduced into the bottle jacket respectively, as a unit. To ensure good and precise positioning of the fastening ring, holding ribs or holding webs for positioning and fastening the ring and the teat respectively may be provided either on the bottom cap itself or on a possible membrane of a valve assembly. In order to achieve a reliable disinfection also of the lower edge region of the fastening ring, it will be beneficial, if the lower edge region is received in the bottom surface in a manner as largely exposed as possible. This will be achieved in a simple and reliable manner, if the membrane has a substantially cylindrical jacket surface on whose inner side several, preferably three, holding webs are provided in a manner distributedly arranged about its periphery and preferably protruding into the interior in a substantially radial direction. The fastening ring can thus be safely and easily positioned on the protruding holding webs of the membrane in a spaced-apart relationship from the bottom surface such that, in an advantageous manner, only small contact faces between the membrane and the fastening ring will be created in the region of the holding webs.

If the teat is placed onto the bottom cap and inserted into the bottle jacket respectively along with the fastening ring as a unit, it is advantageously not required to pull the teat through the opening in the fastening ring upon completion of the disinfection. In conventional disinfection devices, in which these two parts are disinfected separately, the bottle teat is usually seized in the region of its nipple and pulled through the opening provided in the fastening ring, before the fastening ring is screwed onto the bottle jacket or body. By seizing the previously disinfected teat, the bacterial count in an unfavorable manner will be substantially increased again such that an infant or baby fed by the bottle will be contacted by the surfaces having elevated bacterial counts exactly in the lip or tongue region. If, however, the teat—which is usually clampingly held in the opening of the fastening ring—together with the fastening ring are disinfected as a unit, it will be possible upon completion of the disinfecting procedure to seize the fastening ring merely on its outer skirt and, hence, fasten the teat to the teat-side opening prior to feeding, without the user coming into contact with the teat. In order to avoid recontamination, tongs are usually added as an accessory to known disinfection devices, which tongs are meant to be used for mounting the teat. In a disadvantageous manner, such accessories are, however, frequently lost or forgotten at home and not readily available on the way. By contrast, the solution according to the invention does not require such accessories, so that all parts necessary both for disinfection and for the contamination-free assemblage of the bottle will always be reliably available. By avoiding accessories, costs will also be reduced.

According to the method of the invention, the various bottle parts after sterilization are advantageously basically contacted only on those surfaces the sterility of which is not required for feeding. Tests have demonstrated that—provided the fastening ring and the teat are not separated from each other—also those regions where the upper side of a flange of the teat substantially abuts on the lower side of the fastening ring are sufficiently disinfected.

As a rule, a baby bottle also comprises a cover cap to protect the teat from dirtying during transportation and prevent any unintentional escape of liquid. In order to sufficiently disinfect also such cover caps, it will be advantageous if a cover cap is provided, which is placed on the fastening ring in a storage position, removed from the fastening ring in the dispensing position, and placed on the teat-side opening in the disinfection position. In an advantageous manner, the cover cap can thus be placed onto the bottle jacket in the manner of a lid for forming a disinfection chamber, and likewise be reliably disinfected.

If the cover cap comprises internal locking elements, in particular, a snap-in groove or snap-in elements, the cover cap can advantageously be fixed to the bottle jacket without closing the upper opening so as to enable the unopened bottle to be kept or transported in a sterile manner after sterilization, since all the surfaces which are critical in terms of contamination will not be accessible from outside.

In order to enable the simple dosing of a suitable amount of disinfectant, it will be beneficial if the cover cap is used for measuring the disinfectant. To this end, the cover cap may comprise an offset fluid reservoir for receiving the appropriate amount of disinfectant, or, for instance, measuring lines in the manner of a measuring cup.

In order for a sufficient disinfection to be achieved for the individual parts of the bottle, it will be beneficial if between 10 and 40 ml of disinfectant are filled into the bottle jacket. In doing so, it will be advantageous if a lower edge of the fastening ring is arranged above the disinfectant level via, in particular, holding webs after filling into the bottle jacket. If the bottle is heated to a temperature between 100° C. and 120° C., it will be reliably ensured that the disinfectant, usually water, filled into the bottle will boil and evaporate, thus providing the desired disinfection. In this respect, it has turned out to be beneficial if the bottle is heated for a period of between 5 and 3 min as a function of the heating temperature.

Evaporation and boiling will be readily ensured immediately, if the bottle is heated in a microwave oven.

In the following, the invention will be explained in more detail by way of a preferred exemplary embodiment illustrated in the drawings, to which it is, however, not to be restricted. In detail, in the drawings.

Figure 1:
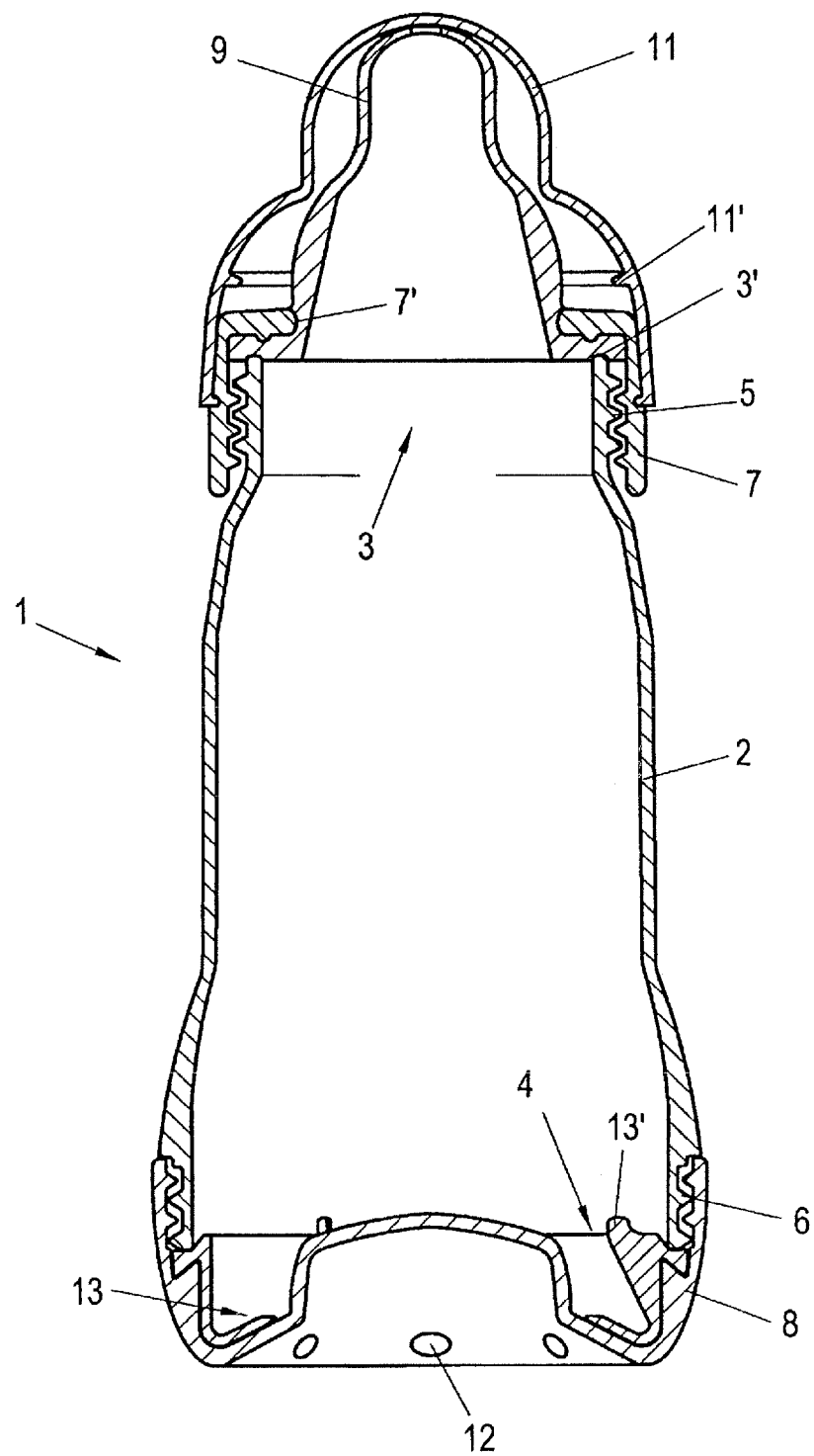
FIG. 1 is a sectional view of a baby bottle known per se, in which the inner periphery of the bottom-side opening is larger than the outer periphery of a fastening ring.

FIG. 1 depicts a baby bottle 1 which comprises a bottle jacket 2 open on both ends and including a teat-side opening 3 as well as a bottom-side opening 4. In the two end regions adjacent the openings 3, 4, of the bottle jacket 2, a male thread 5, 6 is each provided, via which a fastening ring or body 7 and a bottom cap 8 each provided with a mating female thread can be respectively fastened in a simple manner. The fastening ring 7 is provided for clampingly fixing a teat 9, said teat 9 in the lower region of its shaft being clampingly held in an opening 7' of the fastening ring 7 and a flange of the teat 9 being clamped between an upper edge 3' of the bottle jacket 2 and the fastening ring 7. In addition, the bottle 1 comprises a cover cap 11, which is fastened to the fastening ring 7 by a snap-in connection.

The bottom cap 8 in the exemplary embodiment illustrated comprises air intake openings 12, which are covered by a membrane 13 in order to enable the bottom-side air intake into the bottle interior. For the method according to the invention, this bottom valve is, however, not required at all. It is, of course, possible to merely provide a conventional bottom cap 8 without any valve means whatsoever.

In FIG. 1, the bottle 1 is thus shown substantially in its storage position, wherein the transfer of the same into the dispensing position, in which a liquid contained in the bottle 1 can be dispensed, merely requires the prior removal of the cover cap 11. According to the method of the invention, such a bottle 1 can be readily transferred into a disinfection position for disinfection purposes.

Figure 2A:
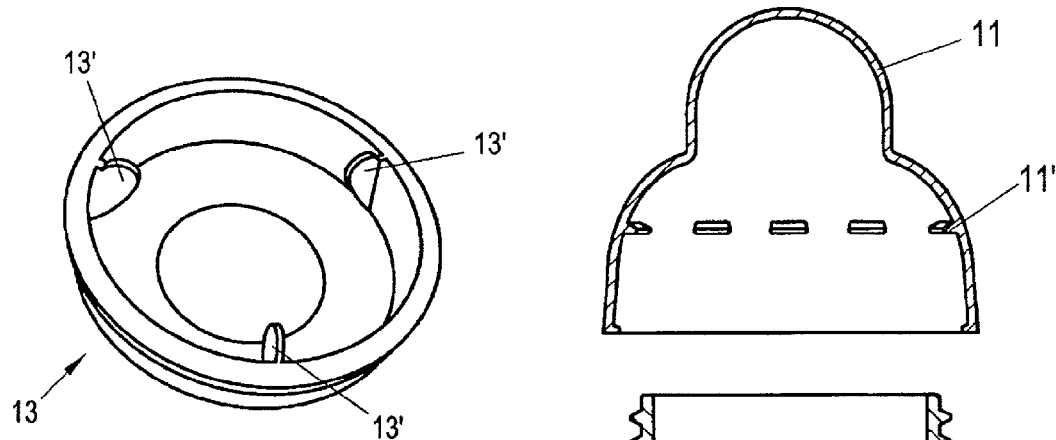
FIG. 2a is a perspective view of a membrane inserted in the bottom cap.
Figure 2:
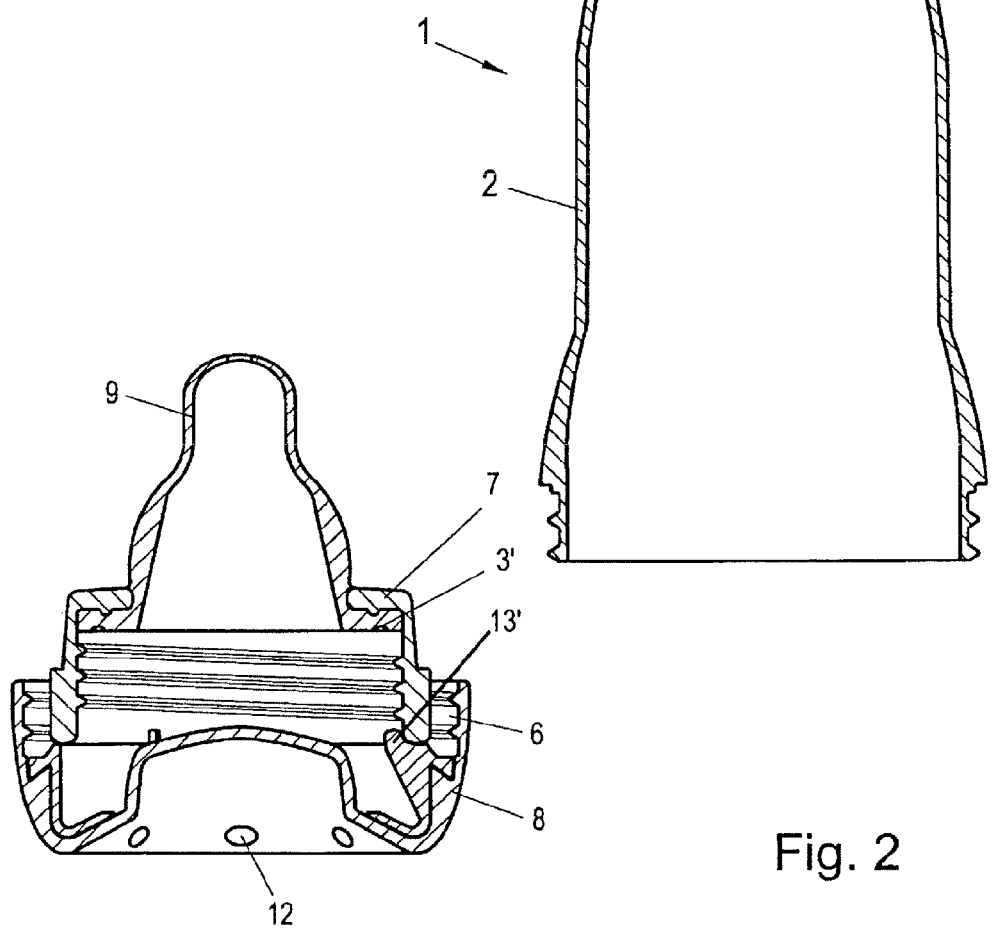
FIG. 2 is a sectional view of the baby bottle according to FIG. 1 in an intermediate position between a dispensing position and a disinfection position, in which a teat plus fastening ring as well as a bottom cap have been screwed off the bottle jacket.
Figure 4:
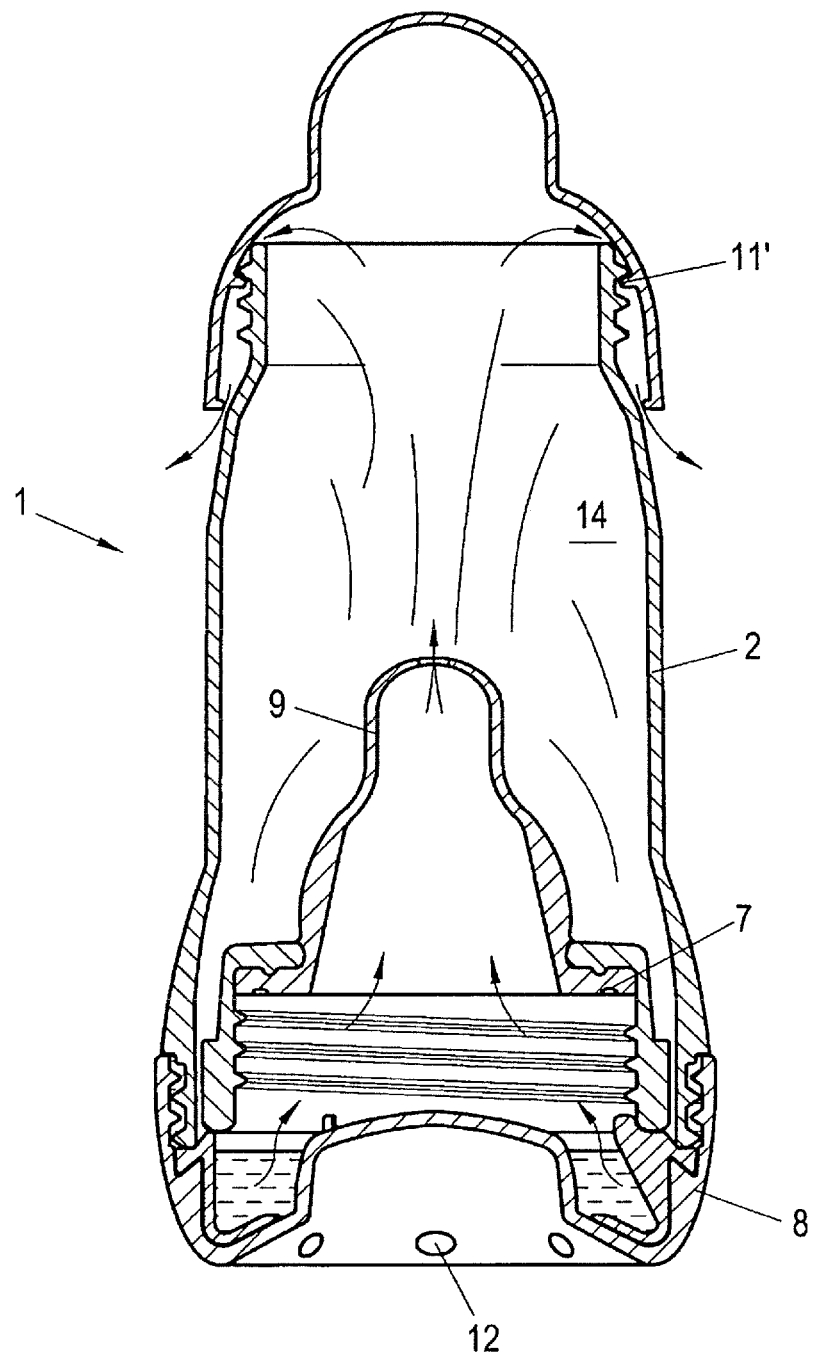
FIG. 4 is a sectional view of the baby bottle in a disinfection position.

FIG. 2 depicts an intermediate position between the storage position illustrated in FIG. 1 and the disinfection position illustrated in FIG. 4. Here, the cover cap 11 was at first removed from the fastening ring 7, and then the fastening ring 7 along with the teat 9 clampingly received in the opening 7' of the fastening ring 7 were screwed off the teat-side opening 3 of the bottle jacket 2. Before or after the fastening ring 7 together with the teat 9 are screwed off the bottle jacket 2, also the bottom cap 8 is screwed off the bottle jacket 2 so as to enable the fastening ring 7 along with the teat 9 clampingly received therein to be placed onto the bottom cap 8 or a membrane 13 received in the bottom cap 8. In doing so, the fastening ring 7 is placed onto the holding webs 13' of the membrane 13, which are illustrated in detail in FIG. 2a. From this it is apparent that the membrane 13 has a substantially cylindrical lateral surface on whose inner side three holding webs 13' are provided, which are arranged in a manner offset by 120° and protruding into the interior. On these holding webs 13' can thus be arranged the fastening ring 7 in a simple and safe manner and in a spaced-apart relationship relative to the bottom surface of the membrane 13. After this, the bottom cap 8 is again screwed onto the bottle jacket 2 along with the fastening ring plus the teat 9 placed therein, such that a disinfection chamber 14 will be formed by the bottle jacket 2 and the bottom cap 8.

Figure 3:
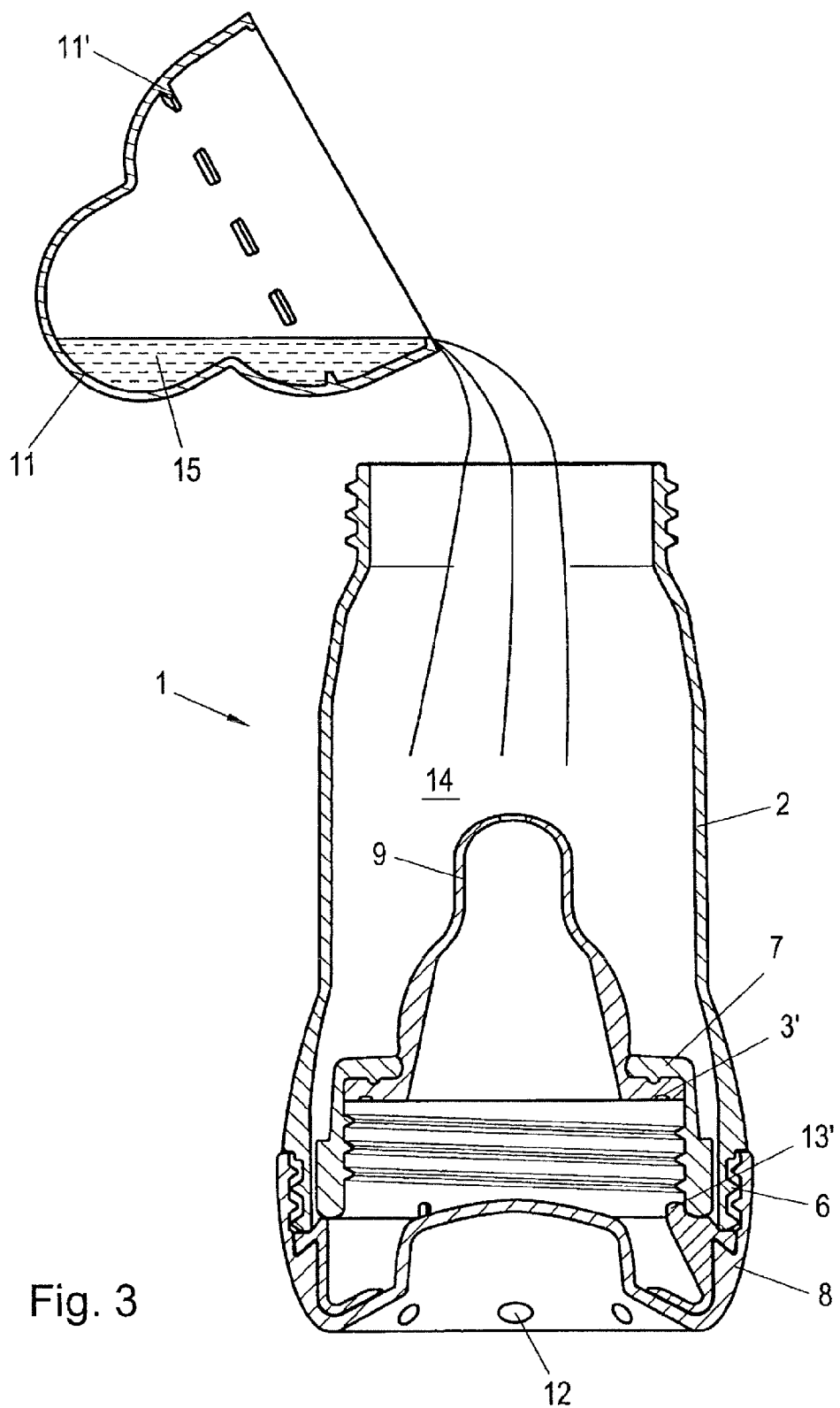
FIG. 3 is a sectional view of the baby bottle according to FIGS. 1 and 2 when filling with water a disinfection chamber formed by the bottle jacket and the bottom cap.

As is apparent from FIG. 3, water 15 for disinfection purposes is subsequently filled into the disinfection chamber 14, preferably by using the cover cap 11, which, in its upside-down position, forms sort of a measuring cup. The cover cap 11 in this case preferably comprises a portion 11' that is recessed relative to the remaining cover cap 11 and has a reception volume of about 10 to 40 ml; this constitutes a suitable amount of water for disinfecting the bottle 1. The cover cap 11 can thus readily serve as sort of a measuring cup for appropriately measuring the water filled into the disinfection chamber 14.

In order to simultaneously provide a disinfection also of the cover cap 11, the latter is finally loosely placed onto the teat-side opening 3 of the bottle jacket 2, as is apparent from FIG. 4. As is also apparent from FIG. 4, the fastening ring 7, by the holding webs 13', is kept in such a position that—after the preferred amount of disinfectant has been introduced—the lower edge of the fastening ring 7 will be located above the disinfectant level; a reliable disinfection will thus also be ensured for the lower edge region of the fastening ring 7.

In this disinfection position, the bottle 1 is then supplied to a heating source, e.g. a microwave oven. To this end, the cover cap 11 may comprise internal locking elements 11', in particular snap-in elements, so as to enable the unopened bottle to be stored or transported in a sterile manner after sterilization, since all surfaces that are critical in terms of contamination will not be accessible from outside.

For the disinfection of baby bottles, a disinfection level of $A_0=600$ according to standard regulations has proved to be appropriate. In order to achieve said disinfection level, an exposure time of 6 s will do at a surface temperature of 100° C.; at lower temperatures, an accordingly longer exposure time will have to be provided. When using 20 ml water for disinfecting a baby bottle, said disinfection level will be achieved within 2 minutes at a microwave power of 800 W. The vapor rising within the disinfection chamber 14 will thus reliably disinfect both the bottom cap 8 and the bottle jacket 2 forming the vapor chamber 14, and the teat 9 received therein as well as the fastening ring 7 and the cover cap 11.

To return the bottle 1 into the storage or dispensing position illustrated in FIG. 1 after disinfection, the bottom cap 8 is screwed off again from the bottle jacket 2, then the fastening ring 7 is screwed onto the teat-side opening 3 of the bottle jacket 2 along with the teat 9 received therein, and subsequently (or before) the bottom cap 8 is again screwed onto the bottom-side opening 4.

Provided the fastening ring 7 is inserted into the vapor chamber 14 along with the teat 9 as a common unit, a substantial advantage of the method according to the invention resides in that, when assembling the bottle 1 into its dispensing position, the teat 9 need not be touched by the user after disinfection. Rather can the fastening ring 7 be seized merely by its cylindrical skirt and the teat 9 be fastened to the bottle jacket 2 without being contacted by an unsterile hand or the like. By contrast, conventional disinfecting methods require the teat 9 to be pulled through the opening 7' provided in the fastening ring 7, wherein the teat 9 is usually seized by unsterile hands in the region of the nipple, i.e. in the region of the tongue and lip contact of the baby or infant, thus dirtying again substantial portions of the previously disinfected parts. This will be reliably prevented by the method according to the invention.

The invention claimed is:

1. A method for disinfecting a bottle, in particular a baby bottle, including a bottle jacket which is open on both ends, wherein, in a dispensing position, a bottom cap is fastened to a bottom-side opening and a teat is fastened to a teat-side opening by a fastening ring, the inner periphery of the bottom-side opening being larger than the outer periphery of the fastening ring, wherein for transfer into a disinfection position, the bottom cap is removed from the bottle jacket respectively, the teat and the fastening ring are placed onto the bottom cap and introduced into the bottle jacket, the bottom cap is attached to the bottom-side opening, a disinfectant, particularly water, is filled into the bottle jacket before the bottle is heated for disinfection.

2. A method according to claim 1, wherein the fastening ring along with the teat are placed onto the bottom cap, and introduced into the bottle jacket respectively, as a unit.

3. A method according to claim 2, wherein the fastening ring is held in its position on the bottom cap, or a membrane, by at least one holding rib or holding web.

4. A method according to claim 3, wherein the membrane has a substantially cylindrical lateral surface on whose inner side several holding webs are provided in a manner distributedly arranged about its periphery and preferably protruding into the interior in a substantially radial direction.

5. A method according to claim 1, wherein a cover cap is provided, which is placed on the fastening ring in a storage position, removed from the fastening ring in the dispensing position, and placed on the teat-side opening in the disinfection position.

6. A method according to claim 1, wherein the cover cap is fixed to the bottle jacket by internal locking elements, in particular, a snap-in groove or snap-in elements.

7. A method according to claim 1, wherein the cover cap is used for measuring the disinfectant.

8. A method according to claim 1, wherein between 10 and 40 ml of disinfectant are filled into the bottle jacket.

9. A method according to claim 1, wherein the bottle is heated to a temperature between 100° C. and 120° C.

10. A method according to claim 1, wherein the bottle is heated in a microwave oven.

* * * * *